(12) United States Patent
Shuttleworth

(10) Patent No.: US 9,116,133 B2
(45) Date of Patent: Aug. 25, 2015

(54) BORE INSPECTION SYSTEM AND METHOD OF INSPECTION THEREWITH

(75) Inventor: Paul S. Shuttleworth, Canal Fulton, OH (US)

(73) Assignee: Federal-Mogul Corporation, Southfield, MI (US)

(*) Notice: Subject to any disclaimer, the term of this patent is extended or adjusted under 35 U.S.C. 154(b) by 1135 days.

(21) Appl. No.: 13/043,977

(22) Filed: Mar. 9, 2011

(65) Prior Publication Data

US 2011/0221887 A1  Sep. 15, 2011

Related U.S. Application Data

(60) Provisional application No. 61/311,805, filed on Mar. 9, 2010.

(51) Int. Cl.
*H04N 7/18* (2006.01)
*G01N 21/954* (2006.01)

(52) U.S. Cl.
CPC ..................... *G01N 21/954* (2013.01)

(58) Field of Classification Search
CPC ............. G01N 21/954; G01N 21/8806; G02B 23/2476; G02B 23/2407; G01B 11/24
USPC ............................. 356/241.1, 237.1, 626, 445
See application file for complete search history.

(56) References Cited

U.S. PATENT DOCUMENTS

| | | | |
|---|---|---|---|
| 3,761,186 A * | 9/1973 | Wason | 356/241.1 |
| 4,467,214 A | 8/1984 | Ito et al. | |
| 4,521,807 A | 6/1985 | Werson | |
| 4,634,273 A | 1/1987 | Farleman et al. | |
| 4,668,983 A | 5/1987 | Werson | |
| 4,702,594 A | 10/1987 | Grant | |
| 4,967,092 A * | 10/1990 | Fraignier et al. | 250/559.07 |
| 5,933,231 A * | 8/1999 | Bieman et al. | 356/241.1 |
| 6,122,063 A | 9/2000 | Berndt et al. | |
| 6,462,815 B1 * | 10/2002 | Drabarek et al. | 356/241.1 |
| 6,661,506 B2 * | 12/2003 | Chang | 356/237.2 |

(Continued)

FOREIGN PATENT DOCUMENTS

| | | |
|---|---|---|
| CN | 101443652 A | 5/2009 |
| DE | 2301714 | 7/1974 |

(Continued)

OTHER PUBLICATIONS

Espacenet English Translation of—Berndt et al. (German Publication No. DE 19746662).*

(Continued)

*Primary Examiner* — Tarifur Chowdhury
*Assistant Examiner* — Mohamed Amara
(74) *Attorney, Agent, or Firm* — Robert L. Stearns; Dickinson Wright, PLLC

(57) ABSTRACT

An imaging system for inspecting an inner surface bounding a component bore is provided along with a method of inspection therewith. The system includes a laser light source configured to emit a laser beam. Further, a camera is configured to image a reflection of the laser beam from the inner surface. At least a first mirror is disposed within the bore. The laser light source is configured to emit the laser beam directly from the laser light source in substantially parallel relation to the central axis incident on the first mirror and the camera is configured to view a reflection of the laser beam from the inner surface.

9 Claims, 2 Drawing Sheets

(56) References Cited

U.S. PATENT DOCUMENTS

| | | | |
|---|---|---|---|
| 6,840,097 | B1 | 1/2005 | Huber et al. |
| 6,934,018 | B2 | 8/2005 | Shaw et al. |
| 7,173,692 | B2 | 2/2007 | Yasuda et al. |
| 7,436,504 | B2 | 10/2008 | Shaw et al. |
| 7,456,973 | B2 | 11/2008 | Steinbichler et al. |
| 7,557,914 | B2 * | 7/2009 | Thompson et al. ........ 356/241.1 |
| 2011/0080588 | A1 * | 4/2011 | Segall .......................... 356/445 |

FOREIGN PATENT DOCUMENTS

| | | |
|---|---|---|
| DE | 2410062 | 9/1975 |
| DE | 3237950 | 5/1984 |
| DE | 3345054 | 6/1984 |
| DE | 19746662 | 2/1999 |
| DE | 102004043209 | 3/2006 |
| FR | 2675903 | 10/1992 |
| GB | 1504974 | 3/1978 |
| JP | 539142 A | 1/1978 |
| JP | 3237308 | 10/1991 |
| JP | 470827 A | 3/1992 |
| JP | 4074912 | 3/1992 |
| JP | 4155206 | 5/1992 |
| JP | H05149885 A | 6/1993 |
| JP | H07113625 A | 5/1995 |
| JP | 8054345 | 2/1996 |
| JP | 10221021 | 8/1998 |
| JP | 11351847 | 12/1999 |
| JP | 11352076 | 12/1999 |
| JP | 367458 U | 4/2000 |
| JP | 2000146856 | 5/2000 |
| JP | 2000162148 | 6/2000 |
| JP | 2000162149 | 6/2000 |
| JP | 2000346814 | 12/2000 |
| JP | 2001034762 | 2/2001 |
| JP | 2001519025 A | 10/2001 |
| JP | 3139297 U | 2/2008 |
| JP | 2009216453 A | 9/2009 |
| JP | 2009244118 | 10/2009 |

OTHER PUBLICATIONS

Espacenet English Translation of—Schanjar et al. (German Publication No. DE102004043209).*

* cited by examiner

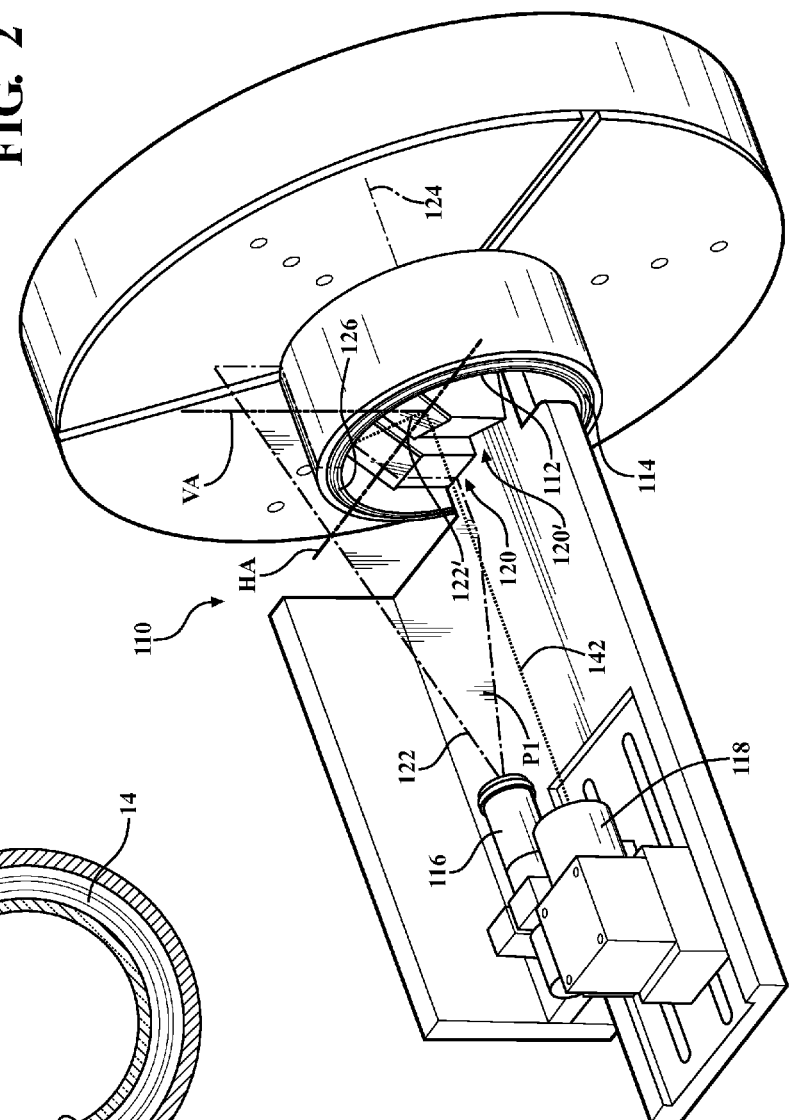
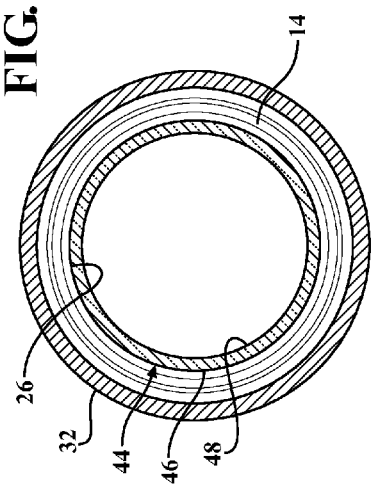

BORE INSPECTION SYSTEM AND METHOD OF INSPECTION THEREWITH

CROSS-REFERENCE TO RELATED APPLICATION

This application claims the benefit of U.S. Provisional Application Ser. No. 61/311,805, filed Mar. 9, 2010, which is incorporated herein by reference in its entirety.

BACKGROUND OF THE INVENTION

1. Technical Field

This invention relates generally to surface inspection systems and methods of inspection thereof, and more particularly to inspection systems and methods for inspecting bores.

2. Related Art

Manufactured parts having annular inner surfaces, e.g., vehicle parts, such as seals, gaskets, or pistons, for example, are typically inspected during manufacture to ensure the inner surfaces meet predetermined specifications. Known inspection systems and methods include measurement systems that make physical contact with the parts during manufacture, such as profilometers, for example. These systems obtain data through relative movement between a stylus and the abutting surface of the part. Although this type of inspection system can provide accurate results, it can result in damage to surface being inspected and the inspection results are generally limited to a small portion of the surface being inspected, and further, can be very time consuming. In addition to damaging the surface being inspected, known inspection systems are generally limited to inspecting relatively small areas, and thus, in many cases the entire surface of the part being inspected in unable to be inspected. Further yet, known bore inspection systems are typically complex, requiring multiple pieces of equipment oriented individually relative to one another, thereby requiring a good deal of set-up time for each different configuration of part being inspected. As such, the known bore inspection systems are generally time consuming to use, and thus costly to operate.

SUMMARY OF THE INVENTION

An imaging system for inspecting an inner surface bounding a component bore is provided. The system includes a laser light source configured to emit a laser beam. Further, a camera is configured to image a reflection of the laser beam from the inner surface. At least a first minor is disposed within the bore. The laser light source is configured to emit the laser beam directly from the laser light source in substantially parallel relation to the central axis incident on the first minor and the camera is configured to view a reflection of the laser beam off the inner surface.

In accordance with a further aspect of the invention, the system includes a light transmisive tube having an outer surface configured to abut the seal bore surface and an inner surface configured to receive the mirror therein.

In accordance with a further aspect of the invention, the system includes a second mirror disposed within the seal bore. The first mirror is configured to reflect the incident laser beam onto the seal bore surface, while the second minor is configured to reflect an image of the seal bore surface to the camera.

In accordance with a further aspect of the invention, a method of inspecting a bore surface of a part is provided. The method includes disposing at least one mirror in the bore. Further, directing a laser beam substantially parallel to a central axis of the bore and reflecting the laser beam off the first minor, onto the inner surface and back onto said at least one minor. Then, capturing an image of the inner surface from the laser beam reflected back onto the at least one minor with a camera.

In accordance with a further aspect of the invention, the method further includes disposing a glass tube in abutment with the bore surface and disposing the at least one mirror within a bore of the glass tube.

In accordance with a further aspect of the invention, the method further includes disposing another mirror within the bore being inspected and reflecting the incident laser beam off one minor onto the bore and reflecting the returning laser beam off the other minor to the camera.

In accordance with yet another aspect of the invention, the method further includes orienting the minors at compound angles relative to one another within the bore to allow the emitted laser beam and the reflected beam to the camera to travel substantially parallel to one another.

BRIEF DESCRIPTION OF THE DRAWINGS

These and other aspects, features and advantages of a bore inspection system and method of inspection therewith in accordance with the invention will become more readily appreciated when considered in connection with the following detailed description of presently preferred embodiments and best mode, appended claims and accompanying drawings, in which:

FIG. 2 is a perspective view of a bore inspection system constructed in accordance with another aspect of the invention; and FIG. 3 is a schematic front view of a housing of the bore inspection system shown having a seal disposed therein with a transparent tube disposed in the seal.

DETAILED DESCRIPTION OF PRESENTLY PREFERRED EMBODIMENTS

Figure 1:
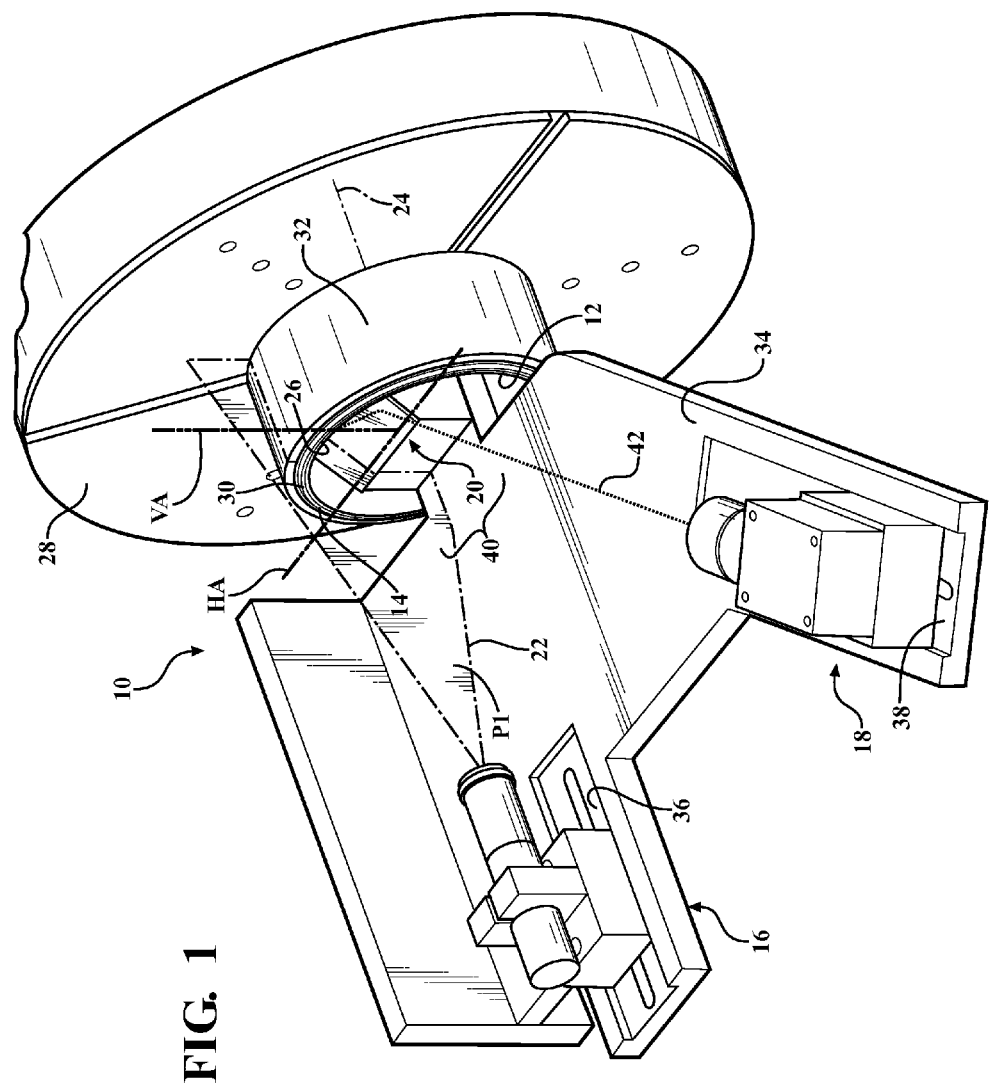
FIG. 1 is a perspective view of a bore inspection system constructed in accordance with one aspect of the invention.

Referring in more detail to the drawings, FIG. 1 illustrates a bore inspection system, referred to hereafter as system 10, configured in accordance with one aspect of the invention to inspect an inner surface 12 bounding a bore of a seal 14, although any component having an inner surface bounding a bore may benefit from being inspected with the system 10. The system 10 includes a laser light source, also referred to as laser beam emitting device 16, an imaging device, such as a camera 18, for example, and at least a first minor 20. The laser emitting device 16 is oriented to transmit a laser beam in the form of a fanned laser beam 22 (fanned in a vertically or substantially vertical plane P1) parallel to or substantially parallel to a horizontal central axis 24 of the seal 14 incident on the first minor 20 that is positioned in radial alignment with the inner surface 12 within the bore of the seal 14. The fanned laser beam 22 reflects off the mirror 20 vertically onto a targeted sealing surface 26 extending across the width of the bore 12, whereupon the laser beam 22 is reflected off the surface 26, as an incident line extending across the full width of the inner surface 12, whereupon the line is reflected back to the minor 20 and is then reflected to and imaged directly and fully by the camera 18 without need of being further reflected by additional minors. Accordingly, the only minor or mirrors are those within the bore in radial alignment with the inner surface 12 of the seal 14. To facilitate imaging the entire surface 26 of the seal bore inner surface 12, the seal 14 can be rotated about its central axis 24 while the mirror 20 remains fixed, wherein the rotation is facilitated via a turntable 28 that is operably fixed to the seal 14.

In the embodiment illustrated in FIG. 1, the seal 14 is mounted in fixed relation in a bore 30 of a carrier, also referred to as housing 32. The housing 32 is fixed to the turntable 28, such that the housing 32 and seal 14 rotate conjointly with the turntable 28 at a selected rotational speed, as desired, during an inspection procedure. It should be recognized that the bore 30 of the housing 32 can be provided having any suitable diameter and width, as preferred, to facilitate fixing components having a variety of different diameters and widths therein.

The laser beam emitter 16, camera 18 and mirror 20 are all fixed relative to one another, and are shown here as being fixed to a common platform 34. The laser beam emitter 16 and camera 18 are shown as being adjustable along respective slide rails 36, 38. The platform 34 extends along a generally horizontal plane and has a reduced width portion 40 sized for a clearance receipt in the bore of the seal 14. The reduced width portion 40, upon being disposed within the bore, does not interfere with or otherwise contact the inner surface 12 bounding the bore, wherein the mirror 20 is fixed to the reduced width portion 40 and also does not interfere with or otherwise contact the inner surface 12. Of course, it should be recognized that the platform 34 need not be provided as a monolithic piece of material, though being formed as a single piece of material facilitates orienting and assuring the laser beam emitter 16, camera 18 and mirror 20 in their desired respective fixed locations relative to one another.

In accordance with another aspect of the invention, as shown in a schematic view of FIG. 3, the system 10 can include a transparent cylindrical tube 44 having an outer surface 46 configured to abut the seal bore inner surface 12 and an inner surface 48 configured to receive the mirror 20 in a clearance fit therein. The outer surface 46 is sized to mimic the shaft size intended for the seal 14, and thus, the images obtained by the camera 18 provide insight as to the contact patch that will be exhibited in actual use between the sealing surface 26 and a running surface of the shaft, or a wear sleeve, if used in application.

With the tube 44 being formed from a light transmissive material, such as a transparent or substantially transparent glass or polymeric material, the laser beam 22 is able to pass through the wall thickness of the tube 44 to provide the camera 18 with an ability to produce a clear and accurate image of the sealing surface 26.

In the embodiment of FIG. 1, the camera 18 is circumferentially or radially offset and focused along an axis 42 that is inclined in an oblique relation to the horizontal central axis 24 of the seal 14. As such, with the laser beam 22 being vertically fanned along the plane P1, the camera 18 is able to view the full reflection of the incident line of the laser beam 22 on the inner surface 12 directly from the flat reflective surface of the first minor 20 without aid of additional mirrors, as long as the width of the body of the seal itself does not obstruct the view path between the first mirror 20 and the lens of the camera 18. The first mirror 20 is tilted from a horizontal plane about 45 degrees from the horizontal central axis 24 about a single horizontal axis HA extending perpendicularly to the laser beam 22, and thus, the laser beam 22 is reflected as a line generally 90 degrees upwardly onto the inner surface 12. If the width of the bore inner surface 12 is wide enough to cause the body of the seal 14 to at least partially interfere with a full viewing of the incident laser line from the first minor 20, then a plurality of minors can be integrated within the seal bore, as shown in FIG. 2, and discussed below.

In FIG. 2, a system 110 is illustrated, wherein the same reference numerals as above, offset by a factor of 100, are used to identify like features. In contrast to the previous system 10, the system 110 incorporates a pair of mirrors 120, 120' disposed within the bore in radial alignment with the inner surface 112 being inspected to facilitate inspecting and imaging a bore 112 having an increased width extending along the central axis 124 in comparison with the width of the previous inner surface 12. The system 110 functions similarly as discussed above to allow the full width of the surface 126 of the bore inner surface 112 to be imaged, however, there are no restrictions placed on the width of the bore 112 capable of being imaged. This is due in part to the use and orientation of the plurality of mirrors 120, 120', and further, to the orientation of a laser beam emitting device 116 and a camera 118 relative to a central axis 124 of the seal 114.

One of the minors, also referred to as first mirror 120, is oriented the same as discussed above, and thus, is tilted to an inclination of about 45 degrees from the central axis 124 about a horizontal axis HA extending perpendicularly to the laser beam 122. However, unlike the previous embodiment, the first minor 120 is sized to reflect the incident laser beam 122, however, it is narrow enough to avoid reflecting the incident line of the laser beam 122 reflecting off the sealing surface 126. As such, the other minor, also referred to as second minor 120', is positioned and sized to reflect a beam 122' of the reflected laser light that is reflected from the sealing surface 126. To facilitate inspecting large depth or width bores, the second minor 120' has a flat reflective surface that is oriented at a compound angle relative to flat reflective surface of the first minor 120, and thus, the flat reflective surfaces of the first and second mirrors 120, 120' are non-parallel to one another. The compound angle is formed by orienting the second mirror 120' to extend in a first plane alone the same 45 degree angle relative to the central axis 124 as the first mirror 120. Thus, the second mirror 120' is first inclined 45 degrees from the central axis 124 about the horizontal axis HA, similarly as the first minor 120. Then, the second minor 120' is also rotated about a vertical axis VA. The rotation of the second minor 120' about the vertical axis VA is over a sufficient number of degrees to cause the beam 122' of the reflected laser light to be imaged fully by the camera 118 along an axis 142 that is parallel, or substantially parallel to the central axis 124. Accordingly, the incident laser beam 122 and the reflected line of the laser beam light 122' travel in parallel or substantially parallel relation to one another. Thus, the camera 118, rather than being oriented in an oblique relation relative to the central axis 124 as in the previous embodiment, is oriented facing along the same direction in generally parallel relation with the laser beam emitting device 116.

In accordance with one method of inspecting a bore using the systems 10, 110 discussed above and illustrated, the method includes disposing at least one minor 20, 120, 120' in a bore of an inner surface 12, 112 being inspected. Then, reflecting a laser beam 22, 122 off the at least one minor 20, 120 onto the bore surface 26, 126. Further, capturing a reflection of the laser beam 22, 122' off the at least one mirror 20, 120' with a camera 18, 118 without the aid of additional mirrors downstream from the minors 20, 120' positioned within the bore 12, 112. When using a plurality of mirrors 120, 120' within the bore 112, the method further includes orienting the minors 120, 120' at a compound angle to one another within the seal bore inner surface 112 and causing the incident and reflected laser beams 122, 122' to travel along substantially parallel axes 124, 142.

The method further includes disposing a glass tube 44 in abutment with the bore surface 26, 126 and disposing the at least one minor 20, 120, 120' within a bore of the glass tube 44.

Obviously, many modifications and variations of the present invention are possible in light of the above teachings. It is, therefore, to be understood that within the scope of the appended claims, the invention may be practiced otherwise than as specifically described.

What is claimed is:

1. An imaging system for inspecting an inner surface bounding a component bore extending about a central axis, comprising:
    a laser light source configured to emit a laser beam;
    a camera configured to capture an image from a reflection of the laser beam from the inner surface;
    a first mirror disposed within the component bore;
    and wherein the laser light source is configured to emit the laser beam directly from the laser light source, without reflection from an intermediate mirror, in substantially parallel relation to the central axis incident on said first mirror, and the camera is external to the component bore being inspected and is configured to capture the image of the inner surface reflected directly from said first mirror.

2. The imaging system of claim 1 wherein said first mirror has a flat reflective surface inclined 45 degrees to a central axis of the bore.

3. The imaging system of claim 1 further comprising a carrier fixed to the component, said carrier being configured for rotation about the central axis.

4. The imaging system of claim 1 wherein said camera is external to the component bore and focused along a path that is inclined relative to the central axis.

5. An imaging system for inspecting an inner surface bounding a component bore extending about a central axis, comprising:
    a laser light source configured to emit a laser beam;
    a camera configured to capture an image from a reflection of the laser beam from the inner surface;
    a first mirror disposed within the component bore;
    a second mirror disposed within the component bore;
    wherein the laser light source is configured to emit the laser beam directly from the laser light source, without reflection from an intermediate mirror, in substantially parallel relation to the central axis incident on said first mirror, and the camera is external to the component bore being inspected and is configured to capture the image of the inner surface reflected directly from a reflective surface of said second mirror; and
    wherein said reflective surface of said second mirror is oriented to reflect light from the inner surface along a path substantially parallel to said central axis to said camera.

6. A method of inspecting an inner surface bounding a bore of a part, comprising:
    disposing a first mirror in the bore;
    directing a laser beam substantially parallel to a central axis of the bore without first reflecting the laser beam and then reflecting the laser beam off the first mirror, onto the inner surface and back onto said first mirror; and
    capturing an image of the inner surface with a camera located outside of the bore, said camera capturing the image from light of the laser beam reflected directly from said first mirror directly to the camera.

7. The method of claim 6 further comprising rotating the part about the central axis while capturing the image 8. The method of claim 6 further comprising orienting the viewing angle of the camera at an inclination relative to the central axis.

9. A method of inspecting an inner surface bounding a bore of a part, comprising:
    disposing a pair of mirrors in the bore with a first one of the pair of mirrors being configured to have a laser beam incident thereon directly from a laser source and a second one of the pair of mirrors being configured to reflect light of the laser beam from the inner surface to a camera;
    directing the laser beam substantially parallel to a central axis of the bore without first reflecting the laser beam, and then reflecting the laser beam off the first mirror onto the inner surface and back onto the second mirror;
    capturing an image of the inner surface with the camera located outside of the bore, said camera capturing the image from light of the laser beam reflected directly from said second mirror; and
    further including orienting the second mirror to reflect the light of the laser beam back to the camera along a path substantially parallel to the central axis.

\* \* \* \* \*

UNITED STATES PATENT AND TRADEMARK OFFICE
CERTIFICATE OF CORRECTION

PATENT NO.       : 9,116,133 B2
APPLICATION NO.  : 13/043977
DATED            : August 25, 2015
INVENTOR(S)      : Paul S. Shuttleworth It is certified that error appears in the above-identified patent and that said Letters Patent is hereby corrected as shown below:

In the Abstract:

Please replace "first minor" with --first mirror--.

In the Specification:

In column 1, lines 48, 51, 61; column 2, lines 2, 3, 4, 13, 14, 50, 55, 62, 64; column 3, lines 55, 65; column 4, lines 23, 26, 27, 39, 40, 41, 55, 57, please replace "minor" with --mirror--. In column 2, lines 16, 64; column 3, line 66; column 4, lines 17, 61, 64, please replace "minors" with --mirrors--.

Signed and Sealed this
Ninth Day of February, 2016

Michelle K. Lee
*Director of the United States Patent and Trademark Office*